United States Patent [19]

Bacon et al.

[11] Patent Number: 5,032,721
[45] Date of Patent: Jul. 16, 1991

[54] ACID GAS MONITOR BASED ON ION MOBILITY SPECTROMETRY

[75] Inventors: Allan T. Bacon, Joppatowne; Julio Reategui, Hunt Valley; Richard C. Getz, Baltimore, all of Md.

[73] Assignee: Environmental Technologies Group, Inc., Baltimore, Md.

[21] Appl. No.: 534,701

[22] Filed: Jun. 1, 1990

[51] Int. Cl.$^5$ .............................................. H01J 49/40
[52] U.S. Cl. .................................... 250/282; 250/287; 250/288
[58] Field of Search ............... 250/282, 286, 287, 288, 250/423 R

[56] References Cited

U.S. PATENT DOCUMENTS

| | | | |
|---|---|---|---|
| 3,717,028 | 2/1973 | Annino et al. | 73/23.36 |
| 4,777,363 | 10/1988 | Eiceman et al. | 250/287 |
| 4,797,554 | 1/1989 | Blanchard et al. | 250/282 |
| 4,950,893 | 8/1990 | Reategui et al. | 250/282 |

OTHER PUBLICATIONS

Bacon et al., "Detection of HF Using Atomspheric Pressure Ionization (API) and Ion Mobility Spectrometry (IMS)", Jun. 3, 1990.

Primary Examiner—Bruce C. Anderson
Attorney, Agent, or Firm—Leonard Bloom

[57] ABSTRACT

An improved method for operating an ion mobility spectrometer (IMS) to enable detection of an acid gas analyte when air is used as the carrier gas and the drift gas in the IMS. A controlled concentration of a dopant substance is added to the air carrier gas stream prior to application of the carrier gas stream. In the IMS, the drift times of the ions generated from the doped air carrier gas differ from the drift times of the ions generated from the acid gas analyte, enabling the identification and quantification of the analyte. The dopants comprise substituted phenol compounds, with methyl salicylate (MS) or 2-hydroxyacetophenone (2-HAP) being preferred.

9 Claims, 3 Drawing Sheets

ACID GAS MONITOR BASED ON ION MOBILITY SPECTROMETRY

FIELD OF THE INVENTION

The present invention relates to a method for detecting acid gasses. More particularly, it relates to a method for detecting acid gasses in air utilizing an Ion Mobility Spectrometer.

BACKGROUND OF THE INVENTION

There is a pressing need in industry for a monitoring system that is capable of identifying and quantifying trace quantities of hazardous gasses escaping into the air. The monitors, located in the vicinity of processing plants and storage facilities, provide early warning of impending danger to plant personnel and the public and enable corrective action to be taken in time to avoid disaster. An ideal monitoring system is capable of operating unattended continuously for extended periods of time without the need for frequent maintenance or calibration. Monitoring systems in present use rely on an electrochemical cells as the sensing element. These systems fall short of the ideal in that they often lack adequate specificity, require frequent maintenance for calibration and replenishment of electrolyte, and are limited to operation at ambient temperatures above 0° C., because of freezing of the electrolyte.

The Ion Mobility Spectrometer (IMS) is an accepted analytical tool capable of identifying and quantifying trace amounts of a substance in a sample. Basically, an IMS comprises an analyzer cell, means for ionizing samples of an analyte admitted to the cell and means for determining the times required for the ions of the various substances present in the cell to traverse a specific length of the cell under the influence of an accelerating electric field and against the force of a stream of drift gas flowing through the cell in a direction opposite to that of the electric field. A stream of purified air may be used as a carrier gas to introduce the analyte sample into the cell and a stream of purified air may also be used as the drift gas. Both the carrier gas and the drift gas are therefore readily available at an installation site in unlimited quantities and no maintenance is required of the sensor other than the occasional replacement of filters for purifying the carrier and drift gasses. An IMS therefore appears to be the ideal sensor for use in a monitoring system.

However, it has been found that an IMS operated in a conventional manner, using air as the carrier and drift gasses, lacks the specificity necessary to detect many of the acid gasses of interest, such as hydrogen fluoride, hydrogen chloride, nitrogen dioxide, and others. The reason for such lack of specificity is that the ion peak characteristic of pure air alone and the ion peak characteristic of the analyte gas in air both arrive at the ion detector of the IMS at virtually the same times. Since the existence of an alarm condition is determined by the amplitude of the ion current detected at a specific arrival time, the pure air ion peak cannot be distinguished from the analyte and air ion peak, when the analyte is an acid gas.

It is an object of the invention to provide a system for monitoring the atmosphere to determine the presence of hazardous gasses therein.

It is another object of the invention to provide such an atmospheric monitoring system which is capable of operating unattended for extended periods of time, without the need for frequent maintenance or calibration, and which will automatically generate an alarm upon the detection of a potentially dangerous condition.

It is a further object of the invention to provide a monitoring system having the above-mentioned attributes and which is specifically responsive to acid gasses as analytes.

It is still another object of the invention to provide a method for operating an Ion Mobility Spectrometer (IMS) which improves the specificity of the IMS for the detection of acid gasses and therefore enables the use of an IMS as a sensor in a system for monitoring the atmosphere for the presence hazardous acid gasses.

It is a specific object of the invention to provide a method for operating an IMS which improves the specificity of the IMS for the detection of hydrogen fluoride.

Other objects and advantages of the invention will become evident as a complete understanding thereof is gained from the detailed description of the invention to follow, and the accompanying drawings.

BRIEF DESCRIPTION OF THE INVENTION

Briefly, the invention comprises a method for operating an IMS in which purified air is used for the carrier gas and the drift gas. A dopant is added to the carrier gas prior to injecting the carrier gas into IMS analyzer cell. In the reaction region of the cell, the dopant and carrier molecules combine to form reactant ions, under the influence of the cell ionization source, possessing drift times that are greater than the drift time possessed by reactant ions formed by the carrier gas alone. The analyte ions formed in the reaction region of the cell possess drift times that are unchanged by the presence of the dopant material in the reaction region. Thus, the IMS can be set to alarm at a particular ion current level occurring at drift times corresponding to the drift times of the analyte ions and no alarm will be generated in the absence of analyte ions.

Dopants selected from the group of substituted phenols have been found to be effective for the purpose of improving the specificity of an IMS for detecting acid gasses in air, particularly, hydrogen fluoride (HF). The two preferred examples of effective dopants disclosed are methyl salicylate (MS) and 2-hydroxyacetophenone (2-HAP).

DETAILED DESCRIPTION OF THE INVENTION

Figure 1:
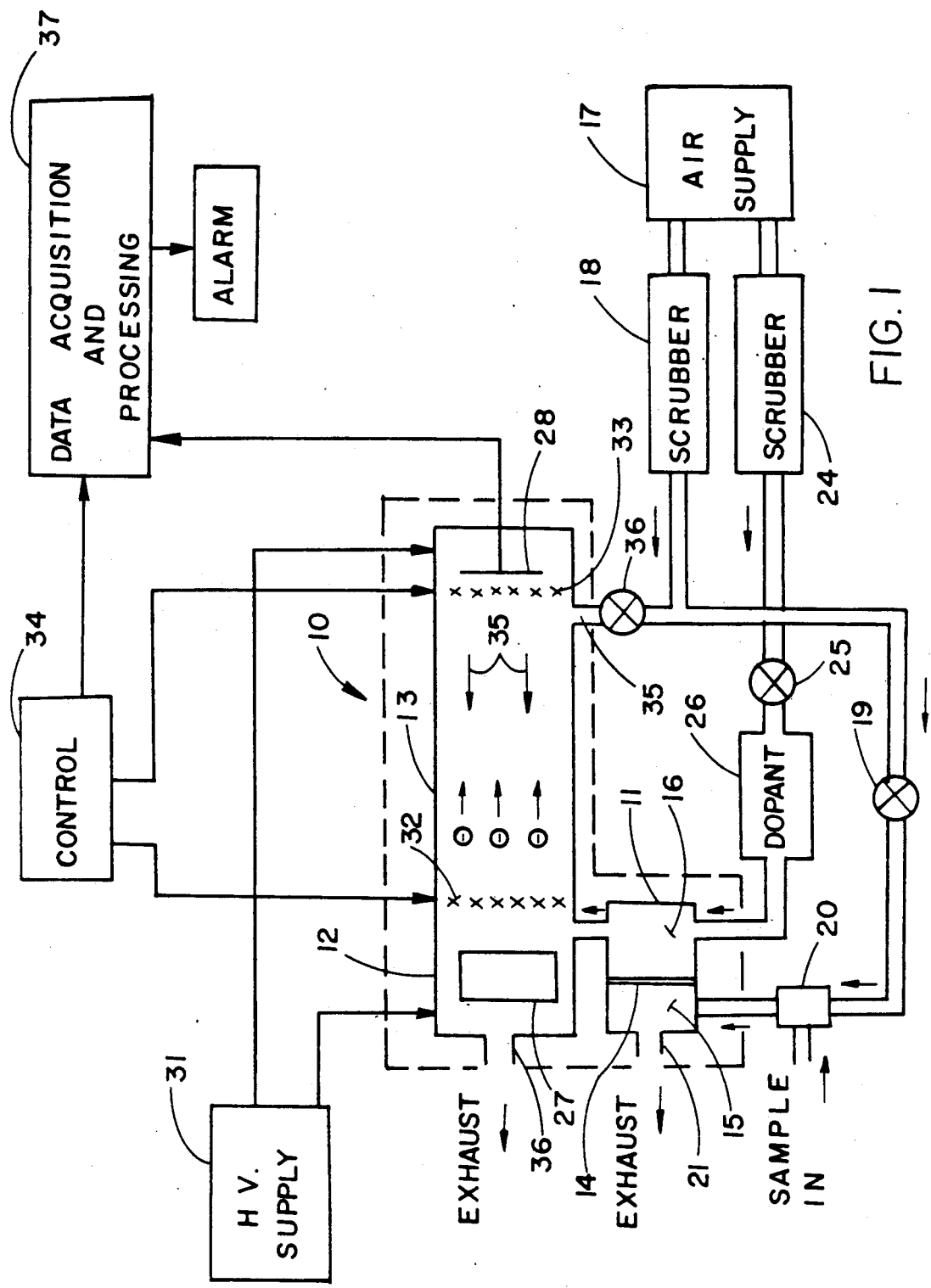
FIG. 1 is a functional block diagram, partially in schematic form, of an Ion Mobility Spectrometer used in the practice of the method of the invention.

Referring to FIG. 1, the apparatus used in the practice of the method of the invention comprises a conventional IMS analyzer cell 10. Cell 10 is divided into an inlet region 11, a reaction region 12 and a drift region 13. Inlet region 11 is partitioned by a permeable membrane 14 into a sample chamber 15 and an inlet chamber 16. Air from a regulated pressure air supply 17 is passed through a scrubber 18, flow regulator 19 and venturi 20 and through sample chamber 15 to an exhaust 21. The air flow through venturi 20 and sample chamber 14 inducts a sample gas, ambient air in this case, into sample chamber 14. Membrane 14 is designed to allow passage of the analyte of interest contained in the sample into inlet chamber 15 while excluding interferant substances from chamber 15. Those substances passing through membrane 14 into chamber 15 are swept from chamber 15 by a carrier gas into the reaction region 12 of analyzer cell 10.

In accordance with the invention, the carrier gas comprises air from air source 17 that is passed through a scrubber 24, primarily to remove water vapor therefrom, flow regulator 25, and a permeation tube 26, where a controlled concentration of dopant is added to the air. Either MS or 2-HAP may be used as a dopant, with MS being preferred.

Reaction region 12 contains a source 27 of $\beta$-particle ionizing radiation which generates product ions from the substances swept into region 12 by the carrier gas. Source 27 is usually formed of a ring of Ni63. The product ions formed in region 12 are urged in the direction of an ion detector 28, located at the end of drift region 13 opposite to reaction region 12, by an electrostatic field applied linearly along regions 12 and 13 by a high voltage supply 31. Reaction region 12 is divided from drift region 13 by a shutter grid 32 and ion detector 28 is separated from drift region 13 by an aperture grid 33. Shutter grid 32 and aperture grid 33 are separately biased by voltages from a control circuit 34. A drift gas, admitted to drift region 13 through port 35, flows continuously through drift region 13 and reaction region 12, exhausting therefrom through exhaust vent 36. The drift gas comprises air from scrubber 18 passed through flow regulator 36 into port 35.

In the conventional mode of operating an IMS for the detection of negative ions, shutter grid 32 is biased negatively for the major part of a scan cycle to block the product ions in reaction region 12 from entering drift region 13. At the beginning of a scan period, the negative bias is briefly removed from shutter grid 32 to admit a cloud of ions into drift region 13. The ions accelerate along the length of drift region 13 under the influence of the electric field and against the force of the counterflowing drift gas, represented by the arrows 35 toward the detector 28.

The product ions of the various substances traverse the drift region in various times, depending upon their charge/molecular size characteristics. If a complete spectrum is to be taken, aperture grid 33 may be neutrally biased so that the arrival times of each of the various ion groups at the detector may be measured. If the IMS is intended to be responsive only to a specific substance, the aperture grid may be biased so as to be repellant to all ions except for a time corresponding to the arrival time that is characteristic of the arrival time of ions of the substance of interest.

Alternatively, the IMS may be operated in the enhancement mode, as disclosed and claimed in U.S. Patent Application Ser. No. 344,128; filed Apr. 27, 1989 by J. A. Reategui et al. for "Method and Apparatus for Enhanced Ion Spectrum Generation and Detection in Ion Mobility Spectrometry", assigned to the assignee of the present application. Briefly, in the enhancement mode, the shutter grid of the IMS is biased open for the major portion of a scan cycle allowing ions to enter the drift region of the analyzer cell continuously upon their generation in the cell reaction region. At the beginning of a scan cycle, the shutter grid is momentarily biased closed, creating a void in the otherwise continuous stream of ions from the reaction region into the drift region. The void traverses the drift region and becomes separated into secondary voids which arrive at the ion detector at different transit times in the same manner that an ion group traverses and becomes separated in an IMS operated in the conventional mode. The substantially steady stream of ions that enters the drift region during the open period of the shutter grid establishes a base line ion current at the detector. The arrival of a separated void at the detector creates a negative peak in the base line current. The arrival time at the detector of a negative peak characterizes the identity of a component substance of the test sample and the amplitude of the negative peak characterizes the concentration of the substance in the test sample. Operation of an IMS in the enhancement mode has the advantages of producing better resolution of the separated ion current peaks and of providing a means permitting continuous calibration of the IMS. Operation of the IMS in the enhancement mode is preferred in the practice of the method of the present invention, although the method is equally applicable to the operation of an IMS in the conventional mode.

Figure 2:
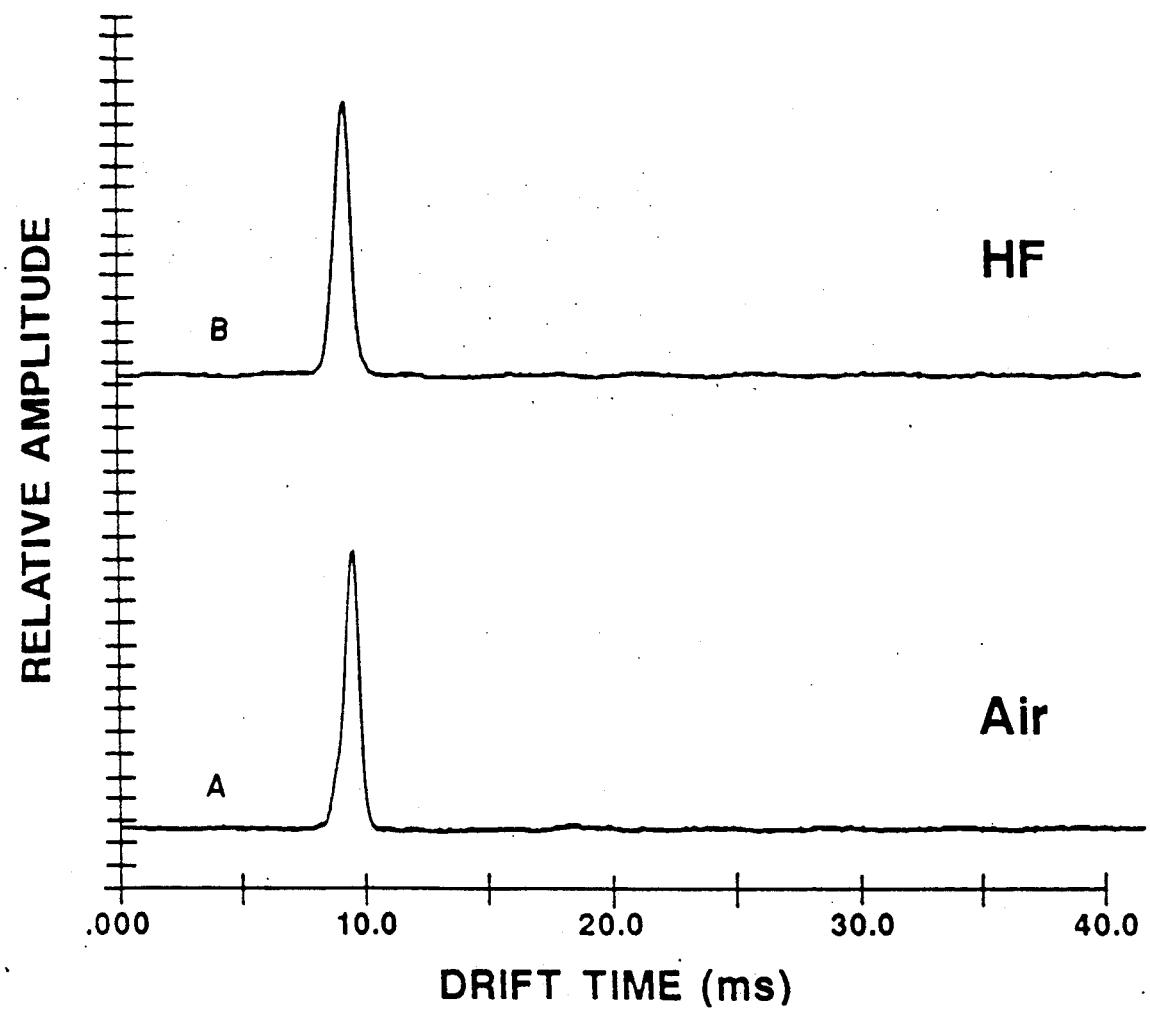
FIG. 2 is a comparative ion mobility spectrograph showing, in line A, the signal response of an IMS to purified air carrier gas; and, in line B, the signal response of an IMS to a sample of HF in purified air carrier gas.

FIG. 2 is a comparative spectrograph showing, in line A, the ion current peak produced when purified air alone is used the carrier gas in an IMS operated in the enhancement mode and no acid gas analyte is present in the test sample. The ion current peak appears at an arrival time of approximately 9.8 milliseconds (ms). Line B of FIG. 2 shows the ion current peak produced when purified air alone is used as the carrier gas in the IMS and an acid gas analyte, specifically hydrogen fluoride, is present in the test sample. The peak in line B occurs at substantially the same arrival time as that in line A, demonstrating the impracticality of using an IMS for the purpose of identifying an acid gas analyte, when purified air alone is used as the carrier gas.

Figure 3:
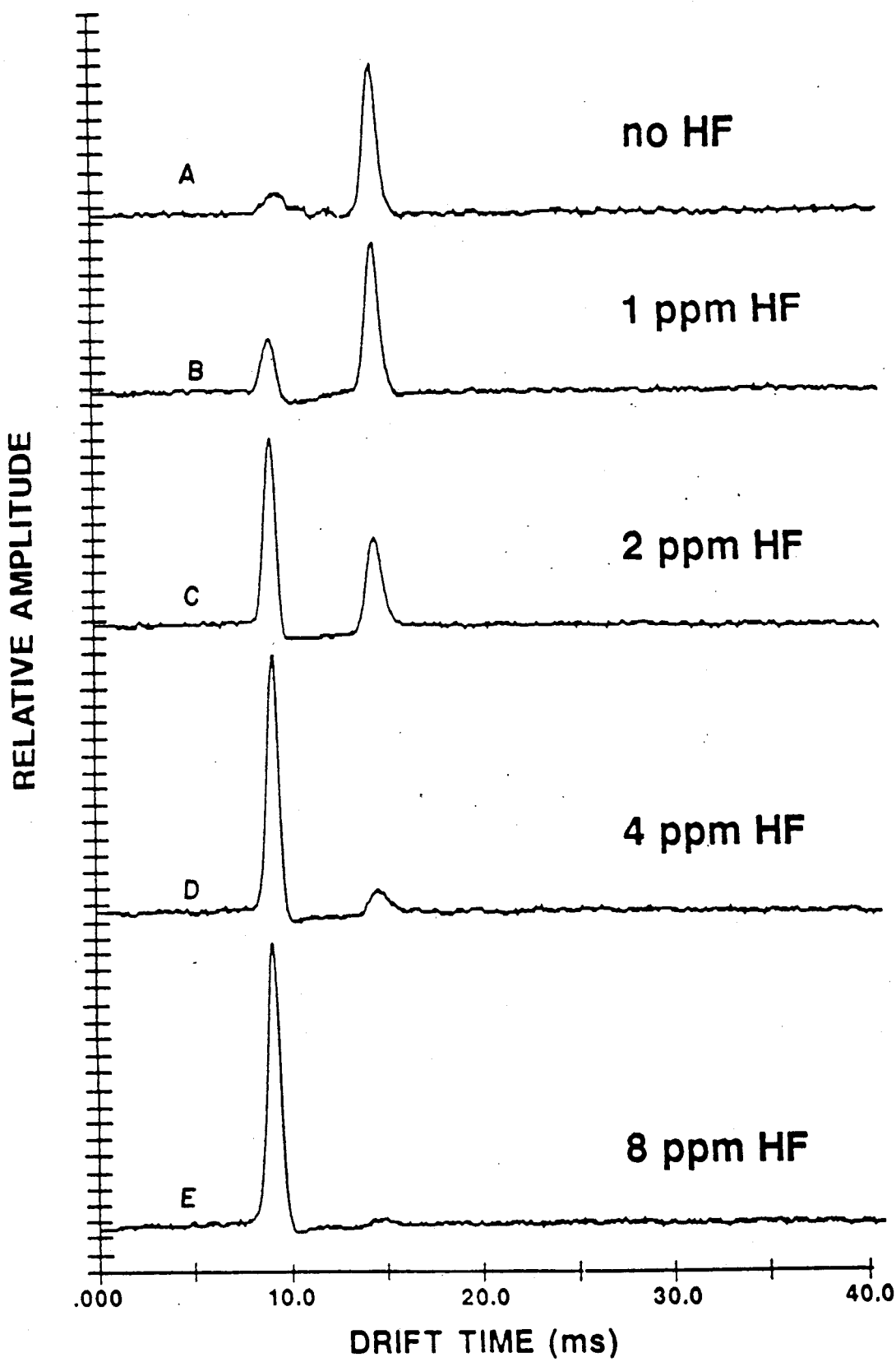
FIG. 3 is a comparative ion mobility spectrograph showing, in line A, the signal response of an IMS to purified air carrier gas containing MS as a dopant and no analyte; and, in lines B–E, showing the signal responses of an IMS to purified air carrier gas containing MS a dopant with respectively increasing concentrations of HF.

FIG. 3 is a comparative spectrograph produced by an IMS operated in the enhancement mode in accordance with the method of the present invention. A small concentration of dopant, specifically MS, has been added to the purified air carrier gas prior to its admission to the IMS. In line A, the arrival time of the principal ion current peak resulting from the air carrier gas with dopant added and no analyte is approximately 15 ms. Lines B-E of FIG. 3 show the results of introducing into the IMS increasingly greater concentrations of analyte, specifically HF, using air with MS added as the carrier gas. The ion current peak resulting from the presence of the analyte remains centered at approximately 9.8 ms for the increasing concentrations. Similarly, the ion current peak resulting from the air carrier gas with MS added remains centered at approximately 15 ms. The decreasing amplitude of the 15 ms peak which occurs as the amplitude of the 9.8 ms peak increases is a manifestation of the principle of conservation of charge, as will be understood by those skilled in the art.

FIG. 3 demonstrates that an IMS operated in accordance with the method of the invention can serve effectively as the sensor in a monitoring system to detect trace amounts of HF in the atmosphere using air as the drift gas and air with MS dopant as the carrier gas. Results similar to those shown in FIG. 3 are obtained when 2-HAP is used as a dopant for the air carrier gas. The method of the invention has also been shown to be effective for the detection of hydrogen chloride and other acid gasses.

The conditions under which the results of FIG. 3 were obtained were as follows:

carrier gas flow—140 cc/min; drift gas flow—250 cc/min; MS concentration—5 ppm; drift region length—3.7 cm.; sampling rate—1 liter/min; reaction region electric field—125 V/cm.; drift region electric field—142 V/cm. inlet membrane—1 mil microporous teflon coated with OV210, available from Altech Associates, Deerfield, Ill.

Again referring to FIG. 1, data acquisition and processing unit 37 collects and averages the peak ion current amplitudes occurring at the arrival times that are characteristic of the analyte for a number of successive scans in order to determine whether the analyte concentration has reached the alarm level. When the analyte is HF in air, the monitoring system described above requires about 10 minutes for the average peak ion current to stabilize at an equilibrium level.

More rapid alarm response can be obtained by processing the data using an algorithm which includes a derivative term in order to predict the equilibrium value of the average peak ion current. A look-up table is first prepared containing values of the ratio of the ion current peaks obtained at the arrival times of the analyte ions and of the doped carrier gas reactant ions for a number of successive scans using known concentrations of analyte.

When a sample having an unknown concentration of analyte is tested, the respective ion current peaks are collected at one second intervals, suitably, and are processed using the following algorithm:

$$T_t = \left(\frac{A_s}{A_r}\right)_t + \sum_{(n=1)}^{(n=60)} \left[\left(\frac{A_s}{A_r}\right)_t - \left(\frac{A_s}{A_r}\right)_{t-1}\right]_n$$

where:
$T_t$ is the table look-up value at time t;
$A_s$ is the peak ion current amplitude at the arrival time of the analyte ion; and
$A_r$ is ion current amplitude at the arrival time of the doped carrier gas ion.

The look-up table will yield the concentration of the analyte when entered at the value obtained for $T_t$ using the above algorithm.

Obviously, variations in the method of the invention are possible in the light of the above teachings. It is therefore to be understood that the invention may be practiced otherwise than as specifically disclosed without departing from the spirit and scope of the appended claims.

The invention claimed is:

1. In a monitoring system having an ion mobility spectrometer for identifying and quantifying constituent substances of a test sample;
    an improved method for operating said spectrometer to enable detection of an acid gas when air is used as the carrier gas and the drift gas in said spectrometer;
    said spectrometer including:
        an analyzer cell having an inlet region, a reaction region, an ionization source in said reaction region, a shutter grid, a drift region, and an ion current detector; and
    means for measuring the transit times through said cell drift region of ions generated in said cell reaction region and released into said cell drift region through said shutter grid;
    said improved method comprising:
    applying a first stream of air to said cell drift region as a drift gas stream;
    introducing a test sample of gas into said analyzer cell inlet region,
    said test sample having an unknown concentration of an acid gas analyte substance therein;
    mixing a dopant substance with a stream of air to create a doped air carrier gas stream;
    applying said doped carrier gas stream to said cell inlet region to carry said test sample into said cell reaction region;
    said dopant substance being of a composition and being added to said air stream in a concentration such that ions generated from said doped carrier gas stream in said cell reaction region possess drift times through said cell drift region which differ from the drift times through said cell drift region of ions generated from said test sample carried into said reaction region by said doped carrier gas stream; and
    measuring the ion currents detected by said cell ion current detector from ions transiting said cell drift region,
    said ion currents being measured at times corresponding to the drift times of ions generated from said analyte substance in said cell reaction region.

2. The improved method as claimed in claim 1, wherein:
    said dopant is comprised by a substituted phenol compound.

3. The improved method as claimed in claim 1, wherein:
    said dopant is comprised by methyl salicylate.

4. The improved method as claimed in claim 3, wherein:
    said acid gas analyte is comprised by hydrogen fluoride.

5. The improved method as claimed in claim 3, wherein:
    said acid gas analyte is comprised by hydrogen chloride.

6. The improved method of claim 3 wherein:
    said concentration of said dopant in said stream of air is from between 3 parts per million and 10 parts per million.

7. The improved method as claimed in claim 1, wherein:
    said dopant is comprised by 2-hydroxyacetophenone.

8. In a monitoring system having an ion mobility spectrometer for identifying and quantifying constituent substances of a test sample;
    an improved method for operating said spectrometer to enable detection of an acid gas when air is used as the carrier gas and the drift gas in said spectrometer;
    said spectrometer including:
        an analyzer cell having an inlet region, a reaction region, an ionization source in said reaction region, a shutter grid, a drift region, and an ion current detector; and means for measuring the transit times through said cell drift region of ions generated in said cell reaction region and released into said cell drift region through said shutter grid;

said improved method comprising:

applying a first stream of air to said cell drift region as a drift gas stream;

introducing a test sample of gas into said analyzer cell inlet region, said test sample having a known concentration of an acid gas analyte substance therein;

mixing a dopant substance with a stream of air to create a doped air carrier gas stream;

applying said doped carrier gas stream to said cell inlet region to carry said test sample into said cell reaction region;

said dopant substance being of a composition and being added to said air stream in a concentration such that ions generated from said doped carrier gas stream in said cell reaction region possess drift times through said cell drift region which differ from the drift times through said cell drift region of ions generated from said test sample carried into said reaction region by said doped carrier gas stream;

measuring the ion currents detected by said cell ion current detector during a sequence t at times corresponding to the drift time of ions generated from said doped carrier gas in said cell reaction region to provide a series of ion current values $A_r$;

measuring the ion currents detected by said cell ion current detector during said sequence t at times corresponding to the drift time of ions generated from said analyte gas in said cell reaction region to provide a series of ion current values $A_s$;

said sequence t beginning at the time of said introduction of said test sample into said analyzer cell an extending until said ion current values $A_s$ have reached an equilibrium value;

processing said values $A_r$ and $A_s$ in accordance with the algorithm:

$$T_t = \left(\frac{A_s}{A_r}\right) + \sum_{(n=1)}^{(n=60)} \left[\left(\frac{A_s}{A_r}\right)_t - \left(\frac{A_s}{A_r}\right)_{t-1}\right]_n$$

repeating said steps of providing sequences of values of $A_r$, providing sequences of values of $A_s$ and processing for different known concentrations of said analyte in said test sample;

compiling a look-up table containing values of $T_t$ computed from said algorithm for said different known concentrations of analyte in said test sample; and thereafter, measuring said ion currents to provide said sequences of $A_r$ and $A_s$ for an unknown concentration of said analyte;

processing said values of $A_r$ and $A_s$ in accordance with said algorithm to obtain a values of $T_t$ for said unknown concentration of analyte; and entering said look-up table with said value of $T_t$ for said unknown concentration of analyte to determine the actual concentration of said unknown concentration of said analyte.

9. The method as claimed in claim 8, wherein:

said dopant substance is methyl salicylate and said acid gas analyte is hydrogen fluoride.

* * * * *